US006583149B1

(12) United States Patent
Giles et al.

(10) Patent No.: US 6,583,149 B1
(45) Date of Patent: Jun. 24, 2003

(54) METHOD FOR THE TREATMENT OR PREVENTION OF VIRAL INFECTION USING NUCLEOSIDE ANALOGUES

(75) Inventors: Francis J. Giles, Houston, TX (US); Jean Bédard, Rosemere (CA); Robert F. Rando, Annandale, NJ (US)

(73) Assignee: BioChem Pharma Inc. (CA)

( * ) Notice: Subject to any disclaimer, the term of this patent is extended or adjusted under 35 U.S.C. 154(b) by 0 days.

(21) Appl. No.: 09/667,326

(22) Filed: Sep. 22, 2000

Related U.S. Application Data
(60) Provisional application No. 60/155,704, filed on Sep. 24, 1999, and provisional application No. 60/155,705, filed on Sep. 24, 1999.

(51) Int. Cl.[7] .................. A01N 43/54; A01N 43/90; A61K 31/505; A61K 31/52
(52) U.S. Cl. .................. 514/274; 514/262; 514/269
(58) Field of Search .................. 514/262, 269, 514/274

(56) References Cited

U.S. PATENT DOCUMENTS

| | | | |
|---|---|---|---|
| 5,565,438 A | 10/1996 | Chu et al. | 514/50 |
| 5,792,772 A | 8/1998 | Chu et al. | 514/274 |
| 5,792,773 A | 8/1998 | Chu et al. | 514/274 |
| 5,817,667 A | 10/1998 | Chu et al. | 514/274 |
| 5,922,867 A | * 7/1999 | Mansour et al. | |
| 5,955,610 A | 9/1999 | Nguyen-Ba et al. | 544/243 |
| 6,022,876 A | 2/2000 | Chu et al. | 514/274 |
| 6,069,250 A | 5/2000 | Mansour et al. | 544/264 |
| 6,069,252 A | 5/2000 | Liotta et al. | 544/317 |
| 6,274,589 B1 | 8/2001 | Chu et al. | 514/274 |

FOREIGN PATENT DOCUMENTS

| | | |
|---|---|---|
| WO | WO 92/18517 | 10/1992 |
| WO | WO 92/20669 | 11/1992 |
| WO | WO 95/07086 | 3/1995 |
| WO | WO 96/07413 | 3/1996 |
| WO | WO 97/21706 | 6/1997 |
| WO | WO 98/20879 | 5/1998 |
| WO | WO 00/47759 | 8/2000 |
| WO | WO 00/57861 | 10/2000 |
| WO | WO 01/06986 | 2/2001 |

OTHER PUBLICATIONS

Mei–Zhen Luo et al., Synthesis and Biological *Evaluation of L– and –D–Configuration 1,3–Dioxolane 5–Azacytosine and 6–Azathymine Nucleosides, Bioorganic & Medicinal Chemistry Letters* 10 (2000), 2145–2148.

M. Arshad Siddiqui et al., "Synthesis of Optically Pure dioxolane Nucleosides and Their Anti–HIV Activity", Abstracts of papers of the National Meeting of the American Chemical Society, vol. 205, 1993, p. P01 XP000910349 Abstract.

Zhengxian Gu et al., "Mechanism ofAction and In Vitro Activityof 1',3'–Dioxolanylpurine Nucleoside Analogues Against Sensitive and Drug–Resistant Human Immunodefciency Virus Type I Variants", Antimicrobial Agents and Chemotherapy Oct. 1999, pp. 2376–2382, vol. 43, No. 10.

International Search Report, International Application No. PCT/CA 00/01094, Apr. 18, 2001.

Nicholas A. Meanwell and Mark Krystal, *Respiratory syncytial virus: recent progress towards the discovery of effective prophylactic and therapeutic agents*, Therapeutic focus (reviews), DDT vol. 5, No. 6, Jun. 2000, pp. 241–252.

Jean Bédard et al. "Comparative Study of the Anti–Human Cytomegalovirus Activities and Toxicities of a Tetrahydrofuran Phosphonate Analogue of Guanosine and Cidofovir" Antimicrobial Agents and Chemotherapy, Mar. 1999, pp. 557–567, vol. 43, No. 3.

Arthur F. Lewis et. al. "Inhibition of Human Cytomegalovirus in Culture by Alkenyl Guanine Analogus of the Thiazolo [4,5–d] Pyrimidine Ring System," Antimicrobial Agents and Chemotherapy, Dec. 1994, p. 2889–2895, vol. 38, No. 12.

Eng–Chun Mar et al. "Some nucleoside analogs with anti–human immunodeficiency virus activity inhibit replication of Epstein–Bar virusus," Antiviral Research 28, (1995) 1–11.

Kryzysztof Bednarski et al. "Inhibitory activities of Herpes Simplex Viruses Type 1 and 2 and Human Cytomegalovirus By Stereoisomers of 2'–Deoxy–3'–Oxa–5(E)–(2–Bromovinyl)Uridines and Their 4'–Thio Analogues," Bioorganic & Medicinal Chemistry Letters, vol. 4, No. 22 pp. 2667–2672, 1994.

Kai–Ming Chou, Marina Kukhanova, and Yung–Chi Cheng "A Noval Action of Human Apurinic/Apyrimidinic Endonuclease" J. Biol. Chem., vol. 275, Issue 40, 31009–31015, Oct. 6, 2000.

Steve Weitman et al. "The New Dioxolane, (–)–2'–Deoxy–3'–oxacytidine (BCH–4556, Troxacitabine), Has Activity Against Pancreatic Human Tumor Xenografts," Clinical Cancer Research vol. 6, 1574–1578, Apr. 2000.

(List continued on next page.)

Primary Examiner—James O. Wilson
Assistant Examiner—Traviss McIntosh
(74) Attorney, Agent, or Firm—Millen, White, Zelano, Branigan, P.C.

(57) ABSTRACT

Compounds of formula I:

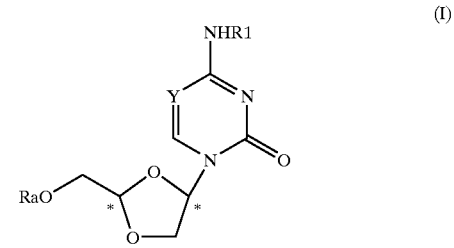

wherein Y, X, R1 and Ra are defined herein are in methods for treating or preventing a viral infections selected from herpes simplex virus, varicella zoster virus, respiratory syncytial virus and cytomegalovirus infections.

32 Claims, No Drawings

OTHER PUBLICATIONS

Shafaat A. Rabbani et al., "Effect of Nucleoside Analogue BCH–4556 on Prostate Cancer Growth and Metastases in Vitro and in Vivo," Cancer Research 58, pp. 3461–3465, Aug. 1, 1998.

P.M. Schwartz et al. "β–L–1,3–Dioxolane–Cytidine: A Novel Nucleoside That Inhibits Proliferation and Induces Differentiation of Keratinocytes in vitro," Skin Pharmacol. Appl Skin Physiol 1998, 11:207–213.

K.L. Grove et al., Beta–L–(–)–Dioxolane Cytidine (β–L–(–)–OddC) As A Potent Compound For The Treatment of Cancer, Nucleosides & Nucleotides, 16(7–9), 1229–1233 (1997).

Salam A. Kadhim et al. "Potent Antitumor Activity of a Novel Nucleoside Analogue, BCH–4556 (β–L–Dioxolane–cytidine), in Human Renal Cell Carcinoma Xenograft Tumor Models," Cancer Research 57, 4803–4810, Nov. 1, 1997.

Kristie L. Grove and Yung–Chi Cheng, "Uptake and Metabolism of the New Anticancer Compound β–L–(–)–Dioxolana–Cytidine in Human Prostate Carcinoma DU–145 Cells," Cancer Research 56, 4187–4191, Sep. 15, 1996.

Migyoung Lee et al. "Dioxolane Cytosine Nucleosides as Anti–hepatitis B Agents," Bioorganic & Medicinal Chemistry Letters, vol. 5, No. 17, pp. 2011–2014, 1995.

Kristie L. Grove et al., "Anticancer Activity of β–L–Dioxolane–cytidine, a Novel Nucleoside Analogue with the Unnatural L. Configuration," Cancer Research 55, 3008–3011, Jul. 15, 1995.

Tarek S. Mansour et al. "Structure–Activity Relationships Among a New Class of Antiviral Heterosubstituted 2',3'–Dideoxynucleoside Analogues," Nucleosides & Nucleotides, 14(3–5), 627–635 (1995).

L.L. Siu et al. "Activity of (–)–2'–deoxy–3'–oxacytidine (BCH–4556) against human tumor colony–forming units," Annals of Oncology 9:885–891, 1998.

Laura E. Moore, et al., "Preclinical pharmacokinetics of β–L–dioxolane–cytidine, a novel anticancer agent, in rats," Cancer Chemother Pharmacol (1997) 39:532–536.

* cited by examiner

METHOD FOR THE TREATMENT OR PREVENTION OF VIRAL INFECTION USING NUCLEOSIDE ANALOGUES

RELATED APPLICATIONS

This application claims priority from U.S. applications Ser. No. 60/155,704 filed on Aug. 24, 1999 and Ser. No. 60/155,705 filed on Aug. 24, 1999 which are herein incorporated by reference.

FIELD OF THE INVENTION

The present invention relates to a method for the treatment or prevention of viral infection using nucleoside analogues.

BACKGROUND OF THE INVENTION

The herpes group of viruses which include cytomegalovirus (CMV), a member of Epstein-Barr virus (EBV), Varicella Zoster virus (VZV), herpes simplex viruses (HSV-1, HSV-2) and human herpes viruses HHV6, HHV7, and HHV8, is recognized as an important pathogen in patients with AIDS. The virus often contributes to the immunosuppression observed in such patients and may cause disseminated disease involving the lungs, gastrointestinal tract, central nervous system, or eyes. CMV retinitis is recognized as a major cause of blindness in patients with AIDS. Also, human cytomegalovirus (HCMV) infection is a major cause of death in AIDS patients. Currently, there are only two approved drugs, ganciclovir, an acyclic guanine nucleoside, and foscarnet, for its treatment. Ganciclovir has exhibited bone marrow suppression as a serious side effect and resistant strains have also been isolated. Foscarnet presents side effects that are associated with its administration such as reversible renal dysfunction, thrombophlebitis at the infusion site, headaches and anemia. Also, foscarnet is not orally bioavailable, limiting its utility in clinical treatment. It is poorly soluble, and large doses are required because of its relatively low potency. Thus, the development of potent and non-toxic anti-CMV agents is therefore highly desirable.

Since their discovery in 1986, the acyclic phoaphonate nucleotide analogs have generated considerable attention as broad spectrum antiviral agents. The guanine analogues HPMPG and PMEG, the adenine analogues HPMPA, and the cytosine analogue HPMPC have been shown to exhibit good anti-HCMV activity and HSV activity. PMEA has also demonstrated in vitro activity against retroviruses such as the human immunodeficiency virus (HIV), as well as DNA viruses such ask herpes simplex virus (HSV), and in vivo activity against murine cytomegalovirus (CMV).

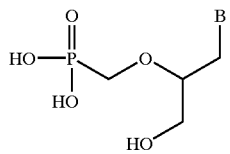

HPMPA, B = adenine
HPMPG, B = guanine
HPMPC, B = cytosine

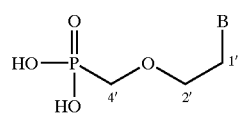

PMEA, B = adenine
PMEG, B = guanine

Unfortunately, in general these compounds present problems in cytotoxicity, particularly, PMEG which is very cytotoxic.

All human herpesviruses have a worldwide distribution and are amongst the most difficult human pathogens to control. Currently, considerable efforts are being directed towards the development of vaccines and antiviral agents that will be active against herpesviruses, particularly Herpes Simplex viruses HSV-1 and HSV-2, and Varicella Zoster virus (VZV). A number of nucleoside and nucleotide derivatives are active against primary and recurrent HSV infection; of these, acyclovir is the most used drug. However, among patients with AIDS, acyclovir-resistant HSV-2 may lead to chronic progressive infections. There is therefore a need for development of potent and non-toxic agents against Herpes viruses.

SUMMARY OF THE INVENTION

The present invention provides a method for treating or preventing a viral infection selected from the group consisting of herpes simplex virus (HSV), varicella zoster virus (VZV), respiratory syncytial virus (RSV) and cytomegalovirus (CMV) in a host comprising administering a therapeutically effective amount of a compound having the formula I:

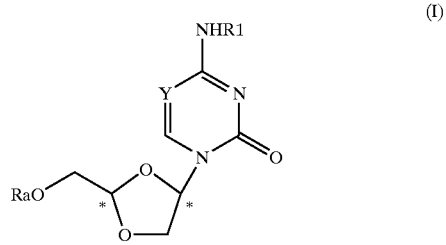

wherein
Y is N or C—X;
X is selected from the group consisting of H, halogen, $C_{1-6}$ alkyl, $C_{2-6}$ alkenyl, $C_{2-6}$ alkynyl, CN, $CF_3$, $N_3$, $NO_2$, $C_{6-10}$ aryl, $C_{6-10}$ heteroaryl and CORb wherein Rb is selected from the group consisting of H, OH, SH, $C_{1-6}$ alkyl, $C_{1-6}$ aminoalkyl, $C_{1-6}$ alkoxy and $C_{1-6}$ thioalkyl;
and Ra is selected from the group consisting of H, $C_{1-6}$ alkyl, $C_{2-6}$ alkenyl, $C_{2-6}$ alkynyl, $C_{6-10}$ aryl, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

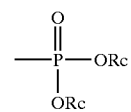

wherein each Rc are independently selected from the group comprising H, $C_{1-6}$ alkyl, $C_{2-6}$ alkenyl, $C_{2-6}$ alkynyl and an hydroxy protecting group,
R1 is selected is selected from the group consisting of H, a $C_{1-6}$ alkyl, $C_{2-6}$ alkenyl, $C_{2-6}$ alkynyl, $C_{6-10}$ aryl, and carbonyl substituted with a $C_{1-6}$ alkyl, $C_{2-6}$ alkenyl, $C_{2-6}$ alkynyl, $C_{6-10}$ aryl,
wherein said compound is in the form of a single enantiomer or a mixture thereof including racemic mixtures.

The present invention provides a method for treating or preventing a viral infection selected from the group consisting of herpes simplex virus (HSV), varicella zoster virus (VZV) and cytomegalovirus (CMV) in a host comprising administering a therapeutically effective amount of a compound having the formula I:

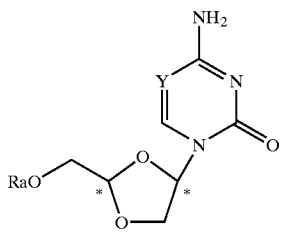

(I)

wherein
Y is N or C—X;
X is selected from the group consisting of H, halogen, $C_{1-6}$ alkyl, $C_{2-6}$ alkenyl, $C_{2-6}$ alkynyl, CN, $CF_3$, $N_3$, $NO_2$, $C_{6-10}$ aryl, $C_{6-10}$ heteroaryl and CORb wherein Rb is selected from the group consisting of H, OH, SH, $C_{1-6}$ alkyl, $C_{1-6}$ aminoalkyl, $C_{1-6}$ alkoxy and $C_{1-6}$ thioalkyl;
and Ra is selected from the group consisting of H, monophosphate, diphosphate, triphosphate, carbonyl substituted with a $C_{1-6}$ alkyl, $C_{2-6}$ alkenyl, $C_{2-6}$ alknyl, $C_{6-10}$ aryl, and

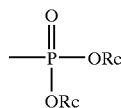

wherein each Rc are independently selected from the group comprising H, $C_{1-6}$ alkyl; $C_{2-6}$ alkenyl, $C_{2-6}$ alkynyl and an hydroxy protecting group,
wherein said compound is in the form of a single enantiomer or a mixture thereof including racemic mixtures.

In another embodiment, there is provided a method for treating or preventing a viral infection selected from the group consisting of herpes simplex virus, varicella zoster virus and cytomegalovirus in a host comprising administering to the host a therapeutically effective amount of at least one compound according to formula I and at least one further antiviral agent.

Still another embodiment, there is provided a pharmaceutical composition for treating or preventing a viral infection selected from the group consisting of herpes simplex virus, varicella zoster virus and cytomegalovirus comprising at least one compound according to formula I together with at least one pharmaceutically acceptable carrier or excipient.

In another embodiment, there is provided a pharmaceutical composition for treating or preventing a viral infection selected from the group consisting of herpes simplex virus, varicella zoster virus and cytomegalovirus comprising at least one compound according to formula I and at least one further antiviral agent.

In another embodiment of the invention is the use of a compound according to formula I for the manufacture of a medicament for treating or preventing a viral infection selected from the group consisting of herpes simplex virus, varicella zoster virus and cytomegalovirus in a host.

In another embodiment, there is provided a method for treating or preventing respiratory syncytial virus in a host comprising administering to the host a therapeutically effective amount of at least one compound according to formula I and at least one further antiviral agent.

Still another embodiment, there is provided a pharmaceutical composition for treating or preventing respiratory syncytial virus comprising at least one compound according to formula I together with at least one pharmaceutically acceptable carrier or excipient.

In another embodiment, there is provided a pharmaceutical composition for treating or preventing respiratory syncytial virus comprising at least one compound according to formula I and at least one further antiviral agent.

In another embodiment of the invention is the use of a compound according to formula I for the manufacture of a medicament for treating or preventing respiratory syncytial virus in a host.

DETAILED DESCRIPTION OF THE INVENTION

The present invention provides a for treating or preventing a viral infection selected from the group consisting of herpes simplex virus, varicella zoster virus respiratory syncytial virus and cytomegalovirus in a host comprising administering a therapeutically effective amount of a compound having the formula I as defined above.

In one embodiment of the invention, Ra is selected from the group comprising H, monophosphate, diphosphate, and triphoschate.

In another embodiment of the invention, Ra is H.
Alternatively X is

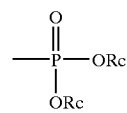

wherein each Rc is independently chosen from H, $C_{1-6}$ alkyl, $C_{2-6}$ alkenyl, $C_{2-6}$ alkynyl or an hydroxy protecting group chosen from S-acylthioethyl ester, acyloxymethyl ester or alkyl methyl carbonate.

In a further embodiment, X is

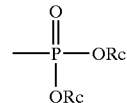

wherein each Rc is independently an hydroxy protecting group chosen from acetyl-2-thioethyl ester, pivaloyloxymethyl ester or isopropyloxycarbonyloxymethyl ester.

In a further embodiment $R_1$ is chosen from H, COOH, $CONH_2$, $C_{1-6}$ alkyl, $C_{2-6}$ alkenyl, $C_{2-6}$ alkynyl or $COOR_d$ wherein $R_d$ is a $C_{1-6}$ alkyl, $C_{2-6}$ alkenyl, or $C_{2-6}$ alkynyl.

In a further embodiment $R_1$ is H, $C_{1-6}$ alkyl or $COOR_d$ wherein $R_d$ is a $C_{1-6}$ alkyl.

In a further embodiment $R_1$ is H, methyl, ethyl or $COOR_d$ wherein $R_d$ is methyl, ethyl.

In a further embodiment $R_1$ is methyl or ethyl.
In a further embodiment $R_1$ is H.
In another embodiment, Y is N.
In another embodiment, Y is C—X.
In another embodiment, X is H, $C_{1-6}$alkyl or halogen.
In another embodiment, X is H, methyl or halogen.
In another embodiment, X is methyl, —C(H)=$CH_2$ and —C≡CH.
In another embodiment, X is H or halogen.
In another embodiment, X is halogen.
In another embodiment, X is H, methyl or F.

In another embodiment, X is H or F.
In another embodiment, X is H.
In another embodiment, X is F.
In one embodiment, a compound of formula I is (−)-cis-2-hydroxymethyl-4-(cytosin-1'-yl)-1,3-dioxclane (β-L-OddC)(compound #1).

In another embodiment, a compound of formula I is (−)-cis-2-hydroxymethyl-4-(5'-fluorocytosin-1'-yl)-1,3-dioxolane (5-FoddC) (compound #2).

In another embodiment, a compound of formula I is (−)-cis-2-hydroxymethyl-4-(5'-azacytosin-1'-yl)-1,3-dioxolane (5-FOddC)(compound #3).

It will be appreciated by those skilled in the art that the compounds of formula (I) contain at least two chiral centres which are marked by an asterisk (*) on formula (I). The compounds of formula (I) thus exist in the form of two different optical isomers (i.e. (+) or (−) enantiomers or β-L and β-D). All such enantiomers and mixtures thereof including racemic mixtures are included within the scope of the invention. The single optical isomer or enantiomer can be obtained by method well known in the art, such as chiral HPLC, enzymatic resolution and the use of chiral auxiliary.

According to one embodiment, compounds of formula I of the present invention are provided substantially in the form of the (−) enantiomer.

According to one embodiment, compounds of formula I of the present invention are provided substantially in the form of the (+) enantiomer.

By "substantially" is meant that there is more one enantiomer then the of the other enantiomer.

In another embodiment, the compounds of formula I of the present invention are at least 95% free of the corresponding (+) enantiomer.

In another embodiment, the compounds of formula I of the present invention are at least 97% free of the corresponding (+) enantiomer.

Still in another embodiment, the compounds of formula I of the present invention are at least 99% free of the corresponding (+) enantiomer.

In another embodiment, the compounds of formula I of the present invention are at least 95% free of the corresponding (−) enantiomer.

In another embodiment, the compounds of formula I of the present invention are at least 97% free of the corresponding (−) enantiomer.

Still in another embodiment, the compounds of formula I of the present invention are at least 99% free of the corresponding (−) enantiomer.

The scope of the present invention also includes compounds which are converted to compounds of formula (I) in vivo. A person skilled in the art would recognize the different technologies available. Non limiting examples include the following PCT publications WO 9945016 and WO 052015 which are incorporated by reference.

There is also provided pharmaceutically acceptable salts of the compounds of formula I of the present invention. By the term pharmaceutically acceptable salts of the compounds of formula (I) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids.

Salts derived from appropriate bases include alkali metal (e.g. sodium), alkaline earth metal (e.g. magnesium), ammonium and $NR_4+$ (where R is $C_{1-4}$ alkyl) salts.

As used in this application the term "alkyl" represents an unsubstituted or substituted (by a halogen, nitro, $CONH_2$, COOH, O—$C_{1-6}$ alkyl, O—$C_{2-6}$ alienyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

The terms "alkenyl" and "alkynyl" represent an alkyl containing at least one unsaturated group (e.g. allyl).

The term "hydroxy protecting group", is well known in the field of organic chemistry. Such protecting groups my be found in T. Greene, *Protective Groups In Organic Synthesis*, (John Wiley & Sons, 1931). Example of hydroxy protecting groups include but are not limited to acetyl-2-thioethyl ester, pivaloyloxymethyl ester and isopropyloxycarbonyloxvmethyl ester.

The term "aryl" represent an unsaturated carbocyclic moiety, optionally mono- or di-substituted with OH, SH, amino, halogen or $C_{1-6}$ alkyl.

The term "heteroaryl" represent an aryl wherein at least one carbon ring atom is substituted by an heteroatom (e.g. N, O, or S).

The term "aminoalkyl" represent an alkyl which is covalently bonded to the adjacent atom through a nitrogen atom.

The term "thioalkyl" represent an alkyl which is covalently bonded to the adjacent atom through a sulfur atom.

The term "alkoxy" represent an alkyl which is covalently bonded to the adjacent atom through an oxygen atom.

As used in this application the abbreviations HPMPA, PMEA, HPMPG, PMEG, and HPMPC respectively mean:

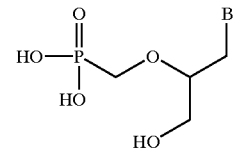

HPMPA, B = adenine
HPMPG, B = guanine
HPMPC, B = cytosine

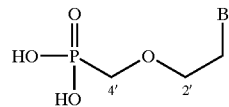

PMEA, B = adenine
PMEG, B = guanine

In accordance with the present invention there is provided a method for treating herpes simplex virus (HSV), varicella zoster virus (VZV), respiratory syncytial virus (RSV) and cytomegalovirus (CMV).

In accordance with the present invention there is provided a method for treating herpes simplex virus, varicella zoster virus and cytomegalovirus (CMV)

In another embodiment, the present invention provides a method for treating HSV-1 and HSV-2.

In another embodiment, the present invention provides a method for treating herpes simplex 1 infection.

In another embodiment, the present invention provides a method for treating herpes simplex 2 infection.

In another embodiment, the present invention provides a method for treating VZV infection.

In another embodiment, the present invention provides a method for treating CMV infection.

In another embodiment, the present invention provides a method for treating human CMV infection.

In another embodiment, the present invention provides a method for treating RSV infection.

The term "host" represent any mammals including humans. In one embodiment, the host is human.

In a further embodiment, there is provided a method to inhibit virus replication in cells infected with a virus selected from herpes simplex virus (HSV), varicella zoster virus (VZV), respiratory syncytial virus (RSV) and cytomegalovirus (CMV).

In a further embodiment, there is provided a method to inhibit virus replication in cells infected with a virus selected from herpes simplex virus (HSV), varicella zoster virus (VZV), respiratory syncytial virus (RSV) and cytomegalovirus (CMV), the method comprising administering to the infected cells an inhibiting amount of a compound of formula (I).

In a further embodiment, there is provided a method for controlling or treating RNA or DNA viral infections selected from herpes simplex virus(HSV), varicella zoster virus (VZV), respiratory syncytial virus (RSV) and cytomegalovirus (CMV), the method comprising administering to the host an RNA or DNA chain terminating amount of as compound of formula (I).

In a further embodiment, there is provided a method for controlling or treating RNA or DNA viral infections the method comprising administering to the host an RNA or DNA chain terminating amount of as compound of formula (I).

The compounds of the present invention can be prepared by methods well known in the art. For example, such methods are described in the following references: U.S. Pat. No. 5,041,449 and PCT publication WO 92/20669 (PCT application PCT/CA92/00211) which are all incorporated by reference.

According to one embodiment, it will be appreciated that the amount of a compound of formula I of the present invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.01 to about 750 mg/kg of body weight per day, preferably in the range of 0.5 to 60 mg/kg/day, most preferably in the range of 1 to 20 mg/kg/day.

The desired dose according to one embodiment is conveniently presented in a single dose or as divided dose administered at appropriate intervals, for example as two, three, four or more doses per day.

In another embodiment, the compound is conveniently administered in unit dosage form; for example containing 10 to 1500 mg, conveniently 20 to 1000 mg, most conveniently 50 to 700 mg of active ingredient per unit dosage form.

According to another embodiment of the present invention, the active ingredient is administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of formula I of the present invention may be administered as the raw chemical, it is preferable according to one embodiment of the invention, to present the active ingredient as a pharmaceutical formulation. The embodiment of the invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

According to one embodiment of the present invention, pharmaceutical formulations include but are not limited to those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods according to this embodiment include the step of bringing into association the active compound with liquid carriers or finely divided solid carriers or both and then, if necessary, shaping the product into the desired formulation.

According to another embodiment, pharmaceutical formulation suitable for oral administration are conveniently presented as discrete units such as capsules, cachets or tablets each containing a predetermined amount of the active ingredient; as a powder or granules. In another embodiment, the formulation is presented as a solution, a suspension or as an emulsion. Still in another embodiment, the active ingredient is presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of formula I according to an embodiment of the present invention are formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds of formula I, according to one embodiment of the present invention, are formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid. In another embodiment, they are presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

According to one embodiment, the formulations suitable for vaginal administration are presented as pessaries, tampons, creams, gels, pastes, foams or sprays containing in addition to the active ingredient such carriers as are known in the art to be appropriate.

For intra-nasal administration the compounds, in one embodiment of the invention, are used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds, according to one embodiment of the invention are conveniently delivered from an insufflator, nebulizer or a pressurized pack or other convenient means of delivering an aerosol spray. In another embodiment, pressurized packs comprise a suitable propellant such as dichlorodifluoromethane, trichlorofluoromethane, dichlorotetrafluoroethane, carbon dioxide or other suitable gas. In another embodiment, the dosage unit in the pressurized aerosol is determined by providing a valve to deliver a metered amount.

Alternatively, in another embodiment, for administration by inhalation or insufflation, the compounds of formula I according to the present invention are in the form of a dry powder composition, for example a powder mix of the compound and a suitable powder base such as lactose or starch. In another embodiment, the powder composition is presented in unit dosage form in, for example, capsules or cartridges or e.g. gelatin or blister packs from which the powder may be administered with the aid of an inhalator or insufflator.

In one embodiment, the above described formulations are adapted to give sustained release of the active ingredient.

In another embodiment, there is provided a method for treating or preventing a RSV, CMV, VZV, or HSV viral infection in a host comprising administering to the host a therapeutically effective amount of at least one compound according to formula I and at least one further antiviral agent.

In another embodiment, there is provided a method for treating or preventing a RSV, CMV, VZV, or HSV viral infection in a host comprising administering to the host a therapeutically effective amount of at least one compound according to formula I and at least one further antiviral agent selected from the group consisting of anti-HSV agents, anti-CMV agents, anti-RSV and anti-VZV agents.

In another embodiment, there is provided a method for treating or preventing a viral infection selected from the group consisting of herpes simplex virus, varicella zoster virus and cytomegalovirus in a host comprising administering to the host a therapeutically effective amount of at least one compound according to formula I and at least one further antiviral agent selected from the group consisting of anti-HSV agents, anti-CMV agents, and anti-VZV agents.

In one embodiment, the antiviral agents are selected from the group consisting of IMPDH (inosine monophosphate dehydrogenase) inhibitors, inhibitors of virus adsorption entry, inhibitors of fusion with host cells, and antisense oligonucleotides.

In one embodiment, the antiviral agents are selected from the group consisting of Acyclovir (ZOVIRAX™), Famciclovir (FAMIVR™), Valacyclovir (VALTREX™), edoxudine (VIROSTA™), ganciclovir, foscamet, cidovir (vistide), Vitrasert, Formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomethoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamide), pyrazofurin (3-[beta-D-ribofuranosyl]-4-hydroxypyrazole-5-carboxamide), 3-Deazaguanine GR-92938X (1-beta-D-ribofuranosylpyrazole-3,4-dicarboxamide), LY253963 (1,3,4-thiadiazol-2-yl-cyanamide), RD3-0028 (1,4-dihydro-2,3-Benzodithiin), CL387626 (4,4'-bis[4,6-di[3-aminophenyl-N,N-bis(2-carbamoylethyl)-sulfonilimino]-1,3,5-triazin-2-ylamino-biphenyl-2,2'-disulfonic acid disodium salt), BABIM (Bis[5-Amidino-2-benzimidazolyl]methane), and NIH351.

In another embodiment, there is provided a method for treating HSV infection in a host comprising administering to the host a therapeutically effective amount of at least one compound according to formula I and at least one further antiviral agent.

In another embodiment, the further antiviral agents are anti-HSV agents.

In another embodiment, the anti HSV agents are selected from the group consisting of Acyclovir (ZOVIRAX™), Famciclovir (FAMIVR™), Valacyclovir (VALTREX™), edoxudine (VIROSTAT™).

Still in another embodiment, the further antiviral agent is Acyclovir.

In another embodiment, there is provided a method for treating VZV infection in a host comprising administering to the host a therapeutically effective amount of at least one compound according to formula I and at least one further antiviral agent.

In another embodiment, the further antiviral agents are anti-VZV agents.

In another embodiment, the anti HSV agents are selected from the group consisting of Acyclovir (ZOVIRAX™), Famciclovir (FAMIVR™), Valacyclovir (VALTREX™), edoxudine (VIROSTAT™).

Still in another erbodiment, the further antiviral agent is Acyclovir.

In another embodiment, there is provided a method for treating CMV infection in a host comprising administering to the host a therapeutically effective amount of at least one compound according to formula I and at least one further antiviral agent.

In another embodiment, the further antiviral agents are anti CMV agents.

In another embodiment, the anti CMV agents are selected from the group consisting of acyclovir, ganciclovir, foscarnet, cidovir (vistide), Vitrasert, Formivirsen, HPMPA, PMEA, HPMPG, PMEG, and HPMPC.

In another embodiment, the anti CMV agents are selected from the group consisting of acyclovir, ganciclovir, forscanet, HPMPA, PMEA, HPMPG, PMEG, and HPMPC.

In another embodiment, the anti CMV agents are selected from the group consisting of acyclovir, forscanet and ganciclovir.

In another embodiment, the anti CMV agents are selected from the group consisting of acyclovir, ganciclovir, foscarnet, cidovir (vistide), Vitrasert, and Formivirsen.

In another embodiment, the anti CMV agents are selected from the group consisting of forscanet and ganciclovir.

In another embodiment, the anti CMV agents is ganciclovir.

In another embodiment, there is provided a method for treating RSV infection in a host comprising administering to the host a therapeutically effective amount of at least one compound according to formula I and at least one further antiviral agent.

In one embodiment, the anti-RSV agent is selected from the group consisting ribavirin, EICAR (5-ethynyl-1-beta-D-riboftiranosylimidazole-4-carboxamide), pyrazofurin (3-[beta-D-ribofuranosyl]-4-hydroxypyrazole-5-carboxamide), 3-Deazaguanine, GR-92938X (1-beta-D-ribofuranosyl-pyrazole-3,4-dicarboxamide), LY253963 (1,3,4-thiadiazol-2-yl-cyanamide), RD3-0028 (1,4-dihydro-2,3-Benzodithiin), CL387626 (4,4'-bis[4,6-di[3-aminophenyl-N,N-bis(2-carbamoylethyl)-sulfonilimino]-1,3,5-triazin-2-ylamino-biphenyl-2,2'-disulfonic acid dissodium salt), BABIM (Bis[5-Amidino-2-benzimidazolyl]methane), and NIH351.

In one embodiment, the anti-RSV agent is ribavirin.

In one embodiment of the present invention, the combinations referred to above are conveniently presented for use in the form of a pharmaceutical composition comprising a combination as defined above together with a pharmaceutically acceptable carrier.

In another embodiment, the individual components of such combinations are administered either sequentially or simultaneously in separate or combined pharmaceutical formulations.

In one embodiment of the present invention, when the compound of formula I or a pharmaceutically acceptable salt thereof is used in combination with a second therapeutic agent, the dose of each compound is either the same as or differ from that when the compound is used alone.

Appropriate doses will be readily appreciated by those skilled in the art.

In a further embodiment of the present invention, there is provided a method for the prevention or for treating or preventing a viral infection selected from the group consisting of respiratory syncytial virus, herpes simplex virus, varicella zoster virus and cytomegalovirus viral infection in organ transplant patient comprising administering to the organ transplant patient a therapeutically effective amount of at least one compound according to formula I. Combinations as defined above can also be used for the prevention or treatment of herpes viral infection in organ transplant patients. Bone marrow transplant is also included in the scope of the present application.

In a further embodiment of the present invention, there is provided a method for the prevention or for treating or preventing a viral infection selected from the group consisting of herpes simplex virus, varicella zoster virus respiratory syncytial virus, cytomegalovirus viral infections in organ transplant patient comprising administering to the organ transplant patient a therapeutically effective amount of at least one compound according to formula I. Combinations as defined above can also be used for the prevention or treatment of herpes viral infection in organ transplant patients.

The compounds of formula I of the present invention can be prepared as follows.

The following examples are provided to illustrate various embodiments of the present invention and shall not be considered as limiting in scope.

EXAMPLE 1

Preparation of (−)-cis-2-Hydroxymethyl-4-(cytosin-1'-yl)-1,3-dioxolane (β-L-OddC) (Compound #1)

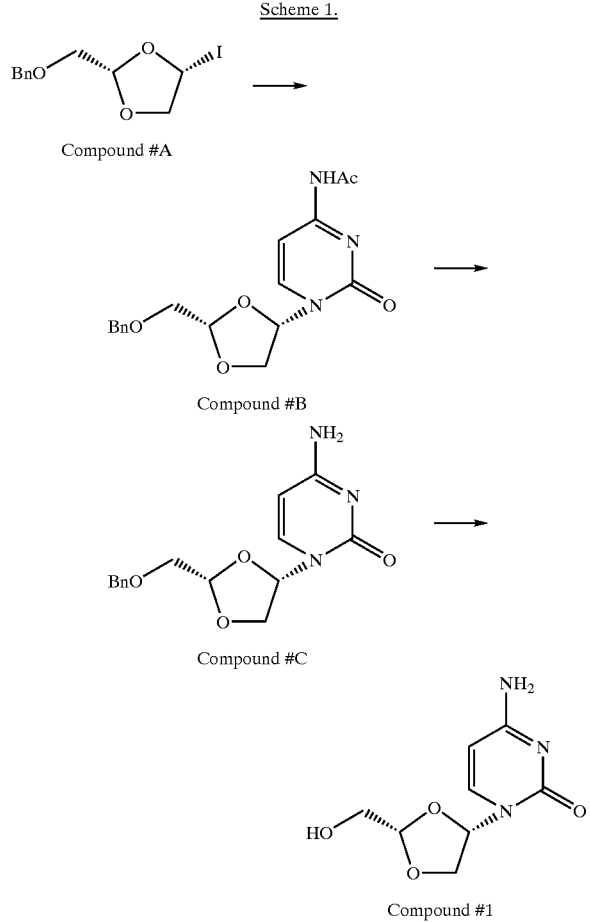

Compound #A
(2S-Benzyloxymethyl-4R-iodo-1,3 Dioxolane and 2S-Benzyloxymethyl-4S-Iodo-1,3 Dioxolane)

A mixture consisting of 2S-benzyloxymethyl-4S acetoxy-1,3 dioxolane and 2S-benzyloxymethyl-4R-acetoxy-1,3 dioxolane in 1:2 ratio (6 g; 23.8 mmol) was dried by azeotropic distillation with toluene in vacuo. After removal of toluene, the residual oil was dissolved in dry dichloromethane (60 ml) and iodotrimethylsilane (3.55 ml; 1.05 eq) was added at −78° C., under vigorous stirring. The dry-ice/acetone bath was removed after addition and the mixture was allowed to warm up to room temperature (15 min.). The ¹H NMR indicated the formation of 2S-benzyloxymethyl-4R-iodo-1,3-dioxolane and 2S-benzyloxymethyl-4S-iodo-1,3 dioxclane.

¹H NMR (300 MHz, CDCl₃) δ 3.65–4.25 (2H, m); 4.50–4.75 (4H, m); 5.40–5.55 (1H, overlapping triplets); 6.60–6.85 (1H, d of d); 7.20–7.32 (5H, m).

Compound #B (D-L-5'-Benzyl-2'-deoxy-3'-oxa-N-4-acetyl-cytidine)

The previously prepared iodo intermediate (Compound #A) in dichloromethane, was cooled down to −78° C. Persylilated N-acetyl cytosine (1.1 eq) formed by reflux in 1,1,1,3,3,3-hexamethyl disilazane (HMDS) and ammonium sulphate followed by evaporation of HMDS was dissolved in 30 ml of dichloromethane and was added to the iodo intermediate. The reaction mixture was maintained at −78° C. for 1.5 hours then poured onto aqueous sodium bicarbonate and extracted with dichloromethane (2×25 ml). The organic phase was dried over sodium sulphate, the solid was removed by filtration and the solvent was evaporated in vacuo to produce 8.1 g of a crude mixture. Based on ¹H NMR analysis, the β-L-5'-benzyl-2'-deoxy-3'-oxacytidine and its α-L isomer were formed in a ratio of 5:1 respectively. This crude mixture was separated by chromatography on silica-gel (5% MeOH in EtOAc) to generate the pure β-L (cis) isomer (4.48 g). Alternatively, recrystallization of the mixture from ethanol produces 4.92 g of pure β isomer and 3.18 g of a mixture of β and α-isomers in a ratio of 1:1.

¹H NMR (300 MHz, CDCl₃) δ 2.20 (3H, S, Ac); 3.87 (2H, m, H-5') 4.25 (2H, m, H-2'); 4.65 (2H, dd, OCC₂Ph); 5.18 (1H, t, H-4'); 6.23 (1H, m, H-1'); 7.12 (1H, d, H-5); 7.30–7.50 (5H, M, Ph); 8.45 (2H, m, NH+H-6).

Compound #C (β-L-5'-Benzyloxy-2'-deoxy-3'-oxacytidine)

The protected β-L isomer (4.4 g) (Compound #B) was suspended in saturated methanolic ammonia (250 ml) and stirred at room temperature for 18 hours in a closed vessel. The solvents were then removed in vacuo to afford the deacetylated nucleoside in pure form.

¹H NMR (300 MHz, CDCl₃) δ 3.85 (2H, m, H-5'); 4.20 (2H, m, H-2'); 4.65 (2H, dd, OCH₂Ph); 5.18 (1H, t, H-4'); 5.43 (1H, d, H-5); 5.50–5.90 (2H, br. S, NH₂); 6.28 (1H, m, H-1'); 7.35–7.45 (5H, m, Ph); 7.95 (1H, d, H-6).

(−)-cis-2-Hydroxymethyl-4-(cytosin-1'-yl)-1,3-dioxclane (β-L-OddC) (Compound #1)

β-L-5'-Benzyl-2'-deoxy-3'-oxacytidine (Compound #C) was dissolved in EtOH (200 ml) followed by addition of cyclohexene (6 ml) and palladium oxide (0.8 g). The reaction mixture was refluxed for 7 hours then it was cooled and filtered to remove solids. The solvents were removed from the filtrate by vacuum distillation. The crude product was purified by flash chromatography on silica-gel (5% MeOH in EtOAc) to yield a white solid (b-L-OddC)(2.33 g; 86% overall yield, $\alpha_D^{22}$=−46.7° (c=0.285; MeOH) m.p.= 192–194° C.).

¹H NMR (300 MHz, DMSO-d₆) δ 3.63 (2H, dd, H-5'); 4.06 (2H, m, H-2'); 4.92 (1H, t, H-4'); 5.14 (1H, t, OH); 5.70 (1H, d, H-5); 6.16 (2H, dd, H-1'); 7.11–7.20 (2H, brS, NH₂); 7.80 (1H, d, H-6) ¹³C NMR (75 MHz, DMSO-d₆) δ 59.5 (C-2'); 70.72 (C-5'); 81.34 (C-4'); 93.49 (C-1'); 104.49 (C-5); 140.35 (C-4); 155.12 (C-6) 165.43 (C-2).

In a similar manner, the following compounds were synthesized:

(−)-cis-2-Hydroxymethyl-4-(5'-fluorocytosin-1'-yl)-1,3-Dioxolane (Compound #2)

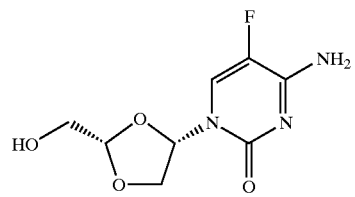

Compound #2

(−)-cis-2-Hydroxymethyl-4-(5'-azacytosin-1'-yl)-1,3-Dioxolane (Compound #3)

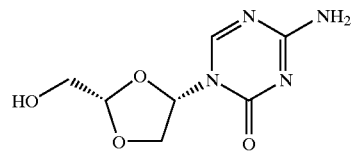

Compound #3

EXAMPLE 2

HSV Activity

Compounds were tested in vitro by the following methods:

HERPES SIMPLEX VIRUS PLAQUE REDUCTION ASSAY

In 12 wells tissue culture dishes, 2×105 Vero34 cells were seeded in 2 mls of DMEM supplemented with 10% PBS. The plate was incubated in 5% CO2/air at 37° C. overnight. The medium was removed and cells were inoculated with 200 PFU of HSV-1 diluted in a final volume of 0.5 ml DMEM supplemented with 2% FES. After adsorption at 37° C. for 1 hour, the viruses were removed and the cell monolayers were overlaid with 1 ml of DMEM-2% FES containing the test compound at final concentrations of 0.1, 1.0, 10, and 50 ug/ml. Acyclovir was used as a positive control. Uninfected and infected untreated monolayers were also included in the assay as controls. All compounds were tested in duplicates. After an incubation at 37° C. in 5% CO2/air for 3 days, cells were fixed with the addition of one volume of formaldehyde 8%/water for 30 min. The formaldehyde/medium was removed and the monolayers were stained with crystal violet 2%/ethanol 20% for few sec. The cells were rinsed with tap water and the monolayers were examined for the presence of plaques under a microscope.

The CD₅₀ value (cytotoxic dose at 50%) was assessed on virus-free control layers of cells to assess the toxicity of the compounds.

Results of the HSV assay are:

| Compounds | HSV-1 IC$_{50}$ | toxicity CD$_{50}$ |
|---|---|---|
| COMPOUND #1 | 1.7 μM | >50 μM |
| COMPOUND #3 | 47–234 μM | — |
| ACYCLOVIR | 13.3 μM | >13.3 μM |

EXAMPLE 3

CMV Activity

CMV Plaque Reduction Assay

The anti-CMV activity of test compounds was evaluated in a plaque reduction assay as follows:

In 12-well tissue culture dishes, 1.5×10E5 or Hs68 cells (human lung fibroblast cell line) were plated per well with 2 ml of DMEM 10% fetal bovine serum and incubated in 5% CO$_2$/air at 37° C. overnight or until cells were ready.

The medium was then removed and the cells inoculated with 0.5 ml (containing 200 pfu/ml diluted in DMEM 2% FBS) of HCMV virus in each well.

After adsorption at 37° C. for 2 hours, the virus was removed and cell monolayers were overlaid (1 ml) with DMEM 2% FBS containing test compounds at various concentrations. The cells were then incubated at 37° C. for 8 days, and then fixed with one volume (1 ml) of formaldehyde 8%/water or PBS 1× for 30 minutes.

The formaldehyde solution was removed and the cell monolayers were stained with crystal violet 2%/EtOH 20% for a few seconds and then rinsed with water.

Monolayers were examined for the presence of plaques under a microscope, the percentage of plaque reduction determined for each compound by comparison with the untreated cells (no test compound) and the 50% inhibitory concentration (IC$_{50}$) established. DHPG was used as a positive control.

Note: DMEM medium contained 1% glutamine and 1% pen/strep

| Compounds | HCMV-1 IC$_{50}$ | toxicity CD$_{50}$ |
|---|---|---|
| COMPOUND #1 | 0.7 μM | >50 μM |
| DHPG | 9.8 μM | >392 μM |

EXAMPLE 4

Cytotoxicity Assay

The cytotoxicity of test compounds was evaluated according to the following procedure:

Flat bottom 96 well plates were plated with 5×1OE3 Vero-34 cells/well and 1×10E4 Hs-68 or Wi-38 cells/well respectively and incubated overnight at 37° C. and 5% CO$_2$/air. After incubation, the supernatant medium was removed and replaced with test compound dilutions in 2% DMEM (150 ul). The cells were then incubated 48 hours in a 5% CO$_2$ incubator at 37° C.

50 μl/well of 10 uCi/ml solution of [3H]-methyl thymidine (specific activity of approx. 2 Ci/mmol) was added to the culture medium and incubated overnight (18 hours) in a 5% CO$_2$ incubator at 37° C.

Cells were then collected onto a fiberglass filter (Printed Filtermat A 1450-421 Wallac) with a Tomtec cell harvester. Suspended cells were collected directly onto filter while for adherent cells, the medium was first removed, then the cells washed with PBS and trypsinized for 2–3 minutes (50 μl trypsin/well) before collecting.

Filters were dried for 1 hour at 37–40° C. and then placed into bags (1450-microbeta #1450-432 Wallac) with 4.5 ml of Betascint and counts obtained with Microbeta 1450 Wallac (protocol 1).

The percent of cell proliferation was determined by comparison to the control (no test compound) and thereby establishing 50% inhibitory concentration is established.

EXAMPLE 5

In Vivo Efficacy of Dioxclane Nucleoside Analogues Against Viral Infections in Humans An elderly male patient with relapsed resistant acute myeloid leukemia was entered in a troxacitabine (compound #1) as phase I Leukemia study. In the early part of the therapy, the patient, known to be immune suppressed, developed severe pneumonias. Subsequent investigations revealed the presence of RSV and CMV viruses. The patient to was maintained in the troxacitabine study and was treated for RSV and CMV viral infections. While immune suppressed patients who develop multiple viral pneumonia exhibit low rates of recovery, this patient did recover from his pneumonias.

The entire disclosures of all applications, patents and publications, cited above, and of corresponding U.S. Provisional Applications Serial Nos. 60/155,704, filed Sep. 24, 1999 and No. 60/155,705, filed Sep. 24, 1999, are hereby incorporated by reference.

We claim:

1. A method for treating a viral infection selected from the group consisting of herpes simplex virus, varicella zoster virus, respiratory syncytial virus and cytomegalovirus in a host, said method comprising administering to said host a therapeutically effective amount of a compound having the formula I:

(I)

wherein

Y is N or C—X;

X is selected from the group consisting of H, halogen, C$_{1-6}$ alkyl, C$_{2-6}$ alkenyl, C$_{2-6}$ alkynyl, CN, CF$_3$, N$_3$, NO$_2$, C$_{6-10}$ aryl, C$_{6-10}$ heteroaryl and CORb;

Rb is selected from the group consisting of H, OH, SH, C$_{1-6}$ alkyl, C$_{1-6}$ aminoalkyl, C$_{1-6}$ alkoxy and C$_{1-6}$ thioalkyl;

Ra is selected from the group consisting of H, C$_{1-6}$ alkyl, C$_{2-6}$ alkenyl, C$_{2-6}$ alkynyl, C$_{6-10}$ aryl,

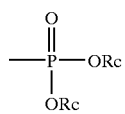

monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and Rc in each case is independently selected from the group comprising H, $C_{1-6}$ alkyl, $C_{2-6}$ alkenyl, $C_{2-6}$ alkynyl and an hydroxy protecting group; and R1 is selected from the group consisting of H, a $C_{1-6}$ alkyl, $C_{2-6}$ alkenyl, $C_{2-6}$ alkynyl, $C_{6-10}$ aryl, and carbonyl substituted with a $C_{1-6}$ alkyl, $C_{2-6}$ alkenyl, $C_{2-6}$ alkynyl, or $C_{6-10}$ aryl; or a pharmaceutically acceptable salt thereof wherein said compound is in the form of a single enantiomer or a mixture of enantiomers.

2. A method of claim 1, wherein said compound is substantially in the form of the (−) enantiomer.

3. A method of claim 1, wherein Ra is H.

4. A method of claim 2, wherein R1 is H.

5. A method of claim 1, wherein Y is C—X.

6. A method of claim 4, wherein Y is C—X and X is H, methyl, or halogen.

7. A method of claim 4, wherein Y is C—X and X is methyl, —C(H)=CH$_2$ or —C≡CH.

8. A method of claim 4, wherein Y is C—X and X is H, methyl or halogen.

9. A method of claim 4, wherein Y is C—X and X is H, methyl or F.

10. A method of claim 4, wherein Y is C—X and X is H or F.

11. A method of claim 4, wherein Y is C—X and X is H.

12. A method of claim 4, wherein Y is C—X and X is F.

13. A method of claim 1, wherein said compound is (−)Cis-2-hydroxymethyl-4-(cytosin-1′-yl)-1,3-Dioxolane.

14. A method of claim 1, wherein said compound is (−)Cis-2-hydroxymethyl-4-(5′-fluorocytosin-1′-yl)-1,3-Dioxolane.

15. A method of claim 1, wherein said compound is (−)Cis-2-hydroxymethyl-4-(5′-azacytosin-1′-yl)-1,3-Dioxolane.

16. A method of claim 1, wherein the herpes simplex virus is HSV-1 or HSV-2.

17. A method of claim 1, wherein the viral infection is a cytomegalovirus infection.

18. A method of claim 1, wherein the viral infection is a respiratory syncytial virus infection.

19. A method of claim 1, wherein the viral infection is a varicella zoster virus infection.

20. A method for treating a viral infection selected from the group consisting of herpes simplex virus, varicella zoster virus, respiratory syncytial virus and cytomegalovirus in a host, said method comprising administering to the host a therapeutically effective amount of at least one compound according to claim 1 and at least one further antiviral agent.

21. A method of claim 20, wherein the further antiviral agent is selected from IMPDH inhibitors, inhibitors of virus adsorption entry, inhibitors of fusion with host cells, and antisense oligonucleotides.

22. A method of claim 20, wherein the further antiviral agent is selected from Acyclovir, Famciclovir, Valacyclovir, edoxudine, ganciclovir, foscarnet, cidovir (vistide), Vitrasert, Formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomethoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamide), pyrazofurin (3-[beta-D-ribofuranosyl]-4-hydroxypyrazole-5-carboxamide), 3-Deazaguanine, GR-92938X (1-beta-D-ribofuranosylpyrazole-3,4-dicarboxamide), LY253963 (1,3,4-thiadiazol-2-yl-cyanamide), RD3-0028 (1,4-dihydro-2,3-Benzodithiin), CL387626 (4,4′-bis[4,6-di[3-aminophenyl-N,N-bis(2-carbamoylethyl)-sulfonilimino]-1,3,5-triazin-2-ylamino-biphenyl-2,2′-disulfonic acid dissodium salt), BABIM (Bis [5-Amidino-2-benzimidazolyl]methane), and NIH351.

23. A method of claim 20, wherein the further antiviral agent is selected from Acyclovir, Famciclovir, Valacyclovir, edoxudine, ganciclovir, foscarnet, cidovir (vistide), ribavirin and Formivirsen.

24. A method of claim 20, wherein the further antiviral agent is selected from Acyclovir, ganciclovir, foscarnet, cidovir (vistide), and ribavirin.

25. A method according to claim 1, wherein said compound is substantially in the form of the (+) enantiomer.

26. A method according to claim 2, wherein said compound is at least 95% free of the corresponding (+) enantiomer.

27. A method according to claim 2, wherein said compound is at least 97% free of the corresponding (+) enantiomer.

28. A method according to claim 2, wherein said compound is at least 99% free of the corresponding (+) enantiomer.

29. A method according to claim 25, wherein said compound is at least 95% free of the corresponding (−) enantiomer.

30. A method according to claim 25, wherein said compound is at least 97% free of the corresponding (−) enantiomer.

31. A method according to claim 25, wherein said compound is at least 99% free of the corresponding (−) enantiomer.

32. A method according to claim 1, wherein said compound is in the form of the racemic mixture.

* * * * *